(12) United States Patent
Yu et al.

(10) Patent No.: US 8,372,395 B2
(45) Date of Patent: Feb. 12, 2013

(54) NANO-EMULSION COMPOSITION OF COENZYME Q10

(75) Inventors: Hyo Gyoung Yu, Gyeonggi-do (KR); Hong Geun Ji, Gyeonggi-do (KR); Soo Dong Kim, Seoul (KR); Hye Kyeong Woo, Seoul (KR)

(73) Assignees: Hwail Pharmaceutical Co., Ltd., Gyeonggi-Do (KR); Hyo Gyoung Yu, Gyeonggi-Do (KR)

( * ) Notice: Subject to any disclaimer, the term of this patent is extended or adjusted under 35 U.S.C. 154(b) by 373 days.

(21) Appl. No.: 12/666,330

(22) PCT Filed: Apr. 24, 2008

(86) PCT No.: PCT/KR2008/002311
§ 371 (c)(1),
(2), (4) Date: Dec. 23, 2009

(87) PCT Pub. No.: WO2009/005215
PCT Pub. Date: Jan. 8, 2009

(65) Prior Publication Data
US 2011/0008305 A1 Jan. 13, 2011

(30) Foreign Application Priority Data
Jul. 4, 2007 (KR) .................. 10-2007-0067217

(51) Int. Cl.
*A61K 31/685* (2006.01)
*A61P 17/18* (2006.01)
(52) U.S. Cl. ..................................... 424/94.1
(58) Field of Classification Search .............. None
See application file for complete search history.

(56) References Cited

U.S. PATENT DOCUMENTS

| 4,824,669 A | 4/1989 | Folkers et al. |
| 2004/0152612 A1* | 8/2004 | Supersaxo et al. ............. 510/407 |
| 2005/0048088 A1* | 3/2005 | Zulli et al. .................... 424/401 |
| 2005/0074445 A1 | 4/2005 | Papas et al. |
| 2006/0198830 A1* | 9/2006 | Shastri et al. ................ 424/94.1 |

FOREIGN PATENT DOCUMENTS

| JP | 2005139122 | 6/2005 |
| WO | 2004080208 | 9/2004 |
| WO | WO 2006/035900 | * 4/2006 |

OTHER PUBLICATIONS

Derwent Abstract of JP 2007077023, 2007, Derwent Accession No. 2007-317817, pp. 1-4.*

* cited by examiner

*Primary Examiner* — Scott Long
*Assistant Examiner* — Sarah Alawadi
(74) *Attorney, Agent, or Firm* — Amall Golden Gregory LLP; Clark G. Sullivan (57) ABSTRACT

The present invention provides a nano-emulsion composition of CoQ10 comprising 5 to 20 wt. % of CoQ10, 1 to 5 wt. % of ethanol, 1 to 5 wt. % of lecithin, 20 to 30 wt. % of caprylic/capric glyceride or vegetable oil(s), 10 to 20 wt. % of glycerin, 1 to 15 wt. % of coemulsifier(s) and the balance of water. The present invention also provides a nano-emulsion composition of CoQ10 comprising 5 to 20 wt. % of CoQ10, 1 to 5 wt. % of ethanol, 20 to 30 wt. % of caprylic/capric glyceride or vegetable oil(s), 1 to 25 wt. % of emulsifier(s), 10 to 20 wt. % of glycerin, and the balance of water. The nano-emulsion composition according to the present invention can preferably improve stability, in vivo penetration, absorptiveness and bioavailability of CoQ10.

6 Claims, 4 Drawing Sheets

NANO-EMULSION COMPOSITION OF COENZYME Q10

TECHNICAL FIELD

The present invention relates to a composition for solubilizing coenzyme Q10 and, more particularly, a nano-emulsion composition for improving stability and bioavailability of coenzyme Q10.

BACKGROUND ART

It is well known that the skin is the outermost organ of the human body and serves to protect the body against external threats or injuries. Ageing of the skin is a naturally occurring physiological condition, which gradually progresses along a programmed course from the time of birth. Skin ageing occurs over all layers of the skin via a complicated mechanism characterized in that oxygen free radicals (hereinafter, referred to as "OFR") are generated by exposure of skin tissues to UV radiation or during a metabolic process, these OFRs attack lipids of cell membranes to induce oxidation thereof and the oxidized lipids destroy the cell membranes, thus resulting in skin ageing.

Demand for methods of preventing or alleviating skin aging tends to be proportional to the quality of life of a society. As one effort to satisfy such demand, studies for development of anti-ageing materials are carried out actively.

Under these circumstances, coenzyme Q10 (hereinafter, referred to as "CoQ10") has attracted a great deal of interest as a substance with anti-ageing and/or anti-oxidation effects. Most CoQ10 is mainly found in the mitochondria, which are frequently referred to as "cellular power plants", and is distributed widely throughout the human body. This substance serves as a strong antioxidant to protect cells from OFRs and assists activity of vitamin E to prevent skin ageing and support cardiovascular functions.

However, although CoQ10 has excellent anti-oxidative effects, CoQ10 is easily degraded due to external environmental factors such as light, heat, oxygen, etc. and is not dissolved in water, general organic solvents and oils, therefore, is used only in restricted applications.

CoQ10 is normally used in the form of a capsule or an emulsion through stabilization in a solution phase using a desired surfactant or emulsifier. However, such stabilization methods may cause coagulation of micelles and/or self-degradation of the capsule or the emulsion due to diffusion of functional ingredients in the solution so that CoQ10 cannot be sufficiently stabilized chemically or physically, thereby restricting industrial application thereof.

Therefore, a great deal of research and study to overcome the problems described above has been conducted, but a reliable or clear solution has not yet been proposed in the related art.

Accordingly, there is a strong need for development of a novel composition to stably solubilize CoQ10 and improve bioavailability of the same.

Technical Problem

The present invention is directed to solve the problems described above in regard to conventional techniques and an object of the present invention is to provide a composition for stabilizing CoQ10 and enhancing bioavailability of the same by nano-emulsification of CoQ10.

Technical Solution

In order to accomplish the above object, the present invention provides a nano-emulsion composition of CoQ10 comprising 5 to 20% by weight (hereinafter, abbrev. to "wt. %") of CoQ10, 1 to 5 wt. % of ethanol, 1 to 5 wt. % of lecithin, 20 to 30 wt. % of caprylic/capric glyceride, 10 to 20 wt. % of glycerin, 1 to 15 wt. % of coemulsifier(s) and the balance of water.

The present invention also provides a nano-emulsion composition of CoQ10 comprising 5 to 20 wt. % of CoQ10, 1 to 5 wt. % of ethanol, 1 to 5 wt. % of lecithin, 20 to 30 wt. % of vegetable oil(s), 10 to 20 wt. % of glycerin, 1 to 15 wt. % of coemulsifier(s) and the balance of water.

The present invention further provides a nano-emulsion composition of CoQ10 comprising 5 to 20 wt. % of CoQ10, 1 to 5 wt. % of ethanol, 20 to 30 wt. % of caprylic/capric glyceride, 1 to 25 wt. % of emulsifier(s), 10 to 20 wt. % of glycerin and the balance of water.

Still further, the present invention provides a nano-emulsion composition of CoQ10 comprising 5 to 20 wt. % of CoQ10, 1 to 5 wt. % of ethanol, 20 to 30 wt. % of vegetable oil(s), 1 to 25 wt. % of emulsifier(s), 10 to 20 wt. % of glycerin and the balance of water.

Mode of Invention

Hereinafter, the present invention will be described in more detail.

"Solubilization" means that a water-insoluble liquid or solid is dissolved in an aqueous solution containing a surfactant or the like to form a thermodynamically stable solution. In other words, solubilization is a process to dissolve a material in a given solvent to form a solution. If the material cannot be solubilized, the material is considered insoluble in the given solvent. During solubilization, the original chemo-physical properties of the material are unchanged. Substances with low solubility in a given solvent can be dissolved in the solvent using a proper additive, which is referred to as a solubilizer.

It is known that solubilization may be affected by certain factors, which include effects due to a chemical structure of the solubilizer such as a length of alkyl groups, types and locations of functional groups, ion effects, a hydrophilic-lipophilic balance and the like, or other effects caused by, for example, solubilizates, temperature, additives, etc.

In accordance with an aspect of the present invention, there is provided a nano-emulsion composition of CoQ10 to solubilize CoQ10, which comprises 5 to 20 wt. % of CoQ10, 1 to 5 wt. % of ethanol, 20 to 30 wt. % of caprylic/capric glyceride or vegetable oil(s), 1 to 25 wt. % of emulsifier(s), 10 to 20 wt. % of glycerin and the balance of water.

In accordance with another aspect of the present invention, there is provided a nano-emulsion composition of CoQ10 to solubilize CoQ10, which comprises 5 to 20 wt. % of CoQ10, 1 to 5 wt. % of ethanol, 1 to 5 wt. % of lecithin, 20 to 30 wt. % of caprylic/capric glyceride or vegetable oil(s), 10 to 20 wt. % of glycerin, 1 to 15 wt. % of coemulsifier(s) and the balance of water.

The present inventive composition can be take the form of a nano-emulsion, which typically includes an inner phase of oil and an outer phase of water so as to capture at least one oil and at least one physiologically active ingredient having low solubility in water. The present invention uses CoQ10 as the active ingredient with low solubility in water, and caprylic/capric glyceride or vegetable oil(s) as the oil captured in the nano-emulsion.

Such vegetable oil(s) preferably includes at least one selected from a group consisting of jojoba oil, macadamia nut oil, sunflower seed oil, olive oil, camellia oil, castor oil and vegetable squalane.

An amount of the active ingredient, that is, CoQ10 used in the present invention preferably ranges from 5 to 20 wt % in view of solubility and precipitation phenomena. If the amount exceeds 20 wt. %, it may occur precipitation of CoQ10. Conversely, less than 5 wt. % of CoQ10 is not enough to ensure beneficial effects thereof.

The caprylic/capric glyceride or the vegetable oil(s) serves as an oil to promote or accelerate penetration or absorption of CoQ10 when the composition is used for beverages or pharmaceutical formulations for oral administration.

The present inventive composition preferably includes the caprylic/capric glyceride or the vegetable oil(s) in an amount ranging from 20 to 30 wt. %. If the amount is less than 20 wt. %, CoQ10 is slightly dissolved or precipitated if the composition is exposed to air for a long time.

The composition of the present invention also includes ethanol as a solubilization additive to dissolve CoQ10, an amount of which preferably ranges from 1 to 5 wt. % to prevent precipitation of CoQ10.

The composition of the present invention additionally includes glycerin, which enables dissolution of a larger amount of insoluble (or slightly soluble) substances even with a relatively small amount of emulsifier.

The present invention may adopt lecithin and coemulsifier(s) in combination or the emulsifier(s) alone.

The present invention preferably uses 1 to 5 wt. % of lecithin which is an amphiphilic emulsifier to improve emulsification stability and accelerate penetration of CoQ10 when administered to a human.

The present invention preferably uses 1 to 15 wt. % of the coemulsifier(s) to further increase stability of the nano-emulsion.

Such emulsifier(s) or coemulsifier(s) contained in the present inventive composition preferably includes at least one selected from a group consisting of Polysorbate 20(polyoxyethylene 20 sorbitan monolaurate); Polysorbate 80(polyoxyethylene 20 sorbitan monooleate); anionic amino acid based emulsifier(s); polyglycerin fatty acid ester; glycerin fatty acid ester; propyleneglycol fatty acid ester; sugar esters; cholesterol; and sodium lauryl sulfate.

The anionic amino acid based emulsifier(s) preferably includes at least one selected from a group consisting of: TEA cocoyl glutamate; sodium glutamate; sodium cocoyl glutamate; magnesium cocoyl glutamate; and sodium lauroyl glutamate.

With regard to the nano-emulsion composition of CoQ10 of the present invention, it is expected that the ranges of constitutional compositions defined above will be preferable. More preferably, the present inventive composition has a specified viscosity ranging from 1.0 to 15 cPs(centipoises) in relation to ethanol and the emulsifier(s) contained in the composition.

ADVANTAGEOUS EFFECTS

The composition of the present invention exhibits excellent solubility in water and excellent in vivo penetration performance. As illustrated in the following experimental examples, an amount of CoQ10 is consistently maintained without precipitation thereof at room temperature (that is, 1 to 30° C.) and at higher temperatures (i.e., 45° C.)

BRIEF DESCRIPTION OF DRAWINGS

The above objects, features and advantages of the present invention will become more apparent to those skilled in the related art in conjunction with the accompanying drawings. In the drawings.

BEST MODE

The present invention will be better understood from the following examples. These examples are not to be construed as limiting the scope of the invention.

EXAMPLES

Example 1

Preparation of a Nano-Emulsion Composition of CoQ10

A nano-emulsion composition of CoQ10 was prepared by using the following components according to the following procedure: CoQ10 and, optionally, lecithin were dissolved in caprylic/capric glyceride (or vegetable oil(s)) and ethanol. After water, glycerine and coemulsifier(s)(or emulsifier(s)) were added to the above solution under sufficient agitation, the resulting mixture was continuously passed five (5) times through a high pressure microfine emulsification machine at 1,000 bar, followed by sterile filtration of the mixture to produce a nano-emulsion composition. This composition was subjected to dispensing and packaging processes to produce a final product.

| | |
|---|---|
| CoQ10 | 5-20 wt. % |
| caprylic/capric glyceride | 20-30 wt. % |
| ethanol | 1-5 wt. % |
| lecithin | 1-5 wt. % |
| glycerin | 10-20 wt. % |
| cholesterol | 1-5 wt. % |
| water | The balance to make a total of 100 wt. % |

Example 2

Preparation of a Nano-Emulsion Composition of CoQ10

A nano-emulsion composition of CoQ10 was prepared by the same procedure as described in Example 1 except that the following constitutional composition for ingredients of the nano-emulsion composition was applied.

| | |
|---|---|
| CoQ10 | 5-20 wt. % |
| caprylic/capric glyceride | 20-30 wt. % |
| ethanol | 1-5 wt. % |
| lecithin | 1-5 wt. % |
| glycerin | 10-20 wt. % |
| cholesterol | 1-5 wt. % |

-continued

| | |
|---|---|
| polysorbate 20 (polyoxyethylene 20 sorbitan monolaurate) | 1-6 wt. % |
| water | The balance to make a total of 100 wt. % |

Example 3

Preparation of a Nano-Emulsion Composition of CoQ10

A nano-emulsion composition of CoQ10 was prepared by the same procedure as described in Example 1 except that the following constitutional composition for ingredients of the nano-emulsion composition was applied.

| | |
|---|---|
| CoQ10 | 5-20 wt. % |
| caprylic/capric glyceride | 20-30 wt. % |
| ethanol | 1-5 wt. % |
| lecithin | 1-5 wt. % |
| glycerin | 10-20 wt. % |
| cholesterol | 1-5 wt. % |
| anionic amino acid based emulsifier (sodium glutamate, magnesium cocoyl glutamate) | 1-6 wt. % |
| water | The balance to make a total of 100 wt. % |

Example 4

Preparation of a Nano-Emulsion Composition of CoQ10

A nano-emulsion composition of CoQ10 was prepared by the same procedure as described in Example 1 except that the following constitutional composition for ingredients of the nano-emulsion composition was applied.

| | |
|---|---|
| CoQ10 | 5-20 wt. % |
| caprylic/capric glyceride | 20-30 wt. % |
| ethanol | 1-5 wt. % |
| lecithin | 1-5 wt. % |
| glycerin | 10-20 wt. % |
| cholesterol | 1-5 wt. % |
| sugar esters | 1-6 wt. % |
| water | The balance to make a total of 100 wt. % |

Example 5

Preparation of a Nano-Emulsion Composition of CoQ10

A nano-emulsion composition of CoQ10 was prepared by the same procedure as described in Example 1 except that the following constitutional composition for ingredients of the nano-emulsion composition was applied.

| | |
|---|---|
| CoQ10 | 5-20 wt. % |
| caprylic/capric glyceride | 20-30 wt. % |
| ethanol | 1-5 wt. % |
| lecithin | 1-5 wt. % |
| glycerin | 10-20 wt. % |
| cholesterol | 1-5 wt. % |
| sodium lauryl sulfate | 1-6 wt. % |
| water | The balance to make a total of 100 wt. % |

Example 6

Preparation of a Nano-Emulsion Composition of CoQ10

A nano-emulsion composition of CoQ10 was prepared by the same procedure as described in Example 1 except that the following constitutional composition for ingredients of the nano-emulsion composition was applied.

| | |
|---|---|
| CoQ10 | 5-20 wt. % |
| caprylic/capric glyceride | 20-30 wt. % |
| ethanol | 1-5 wt. % |
| lecithin | 1-5 wt. % |
| glycerin | 10-20 wt. % |
| polysorbate 80) (polyoxyethylene 20 sorbitan monooleate) | 1-6 wt. % |
| water | The balance to make a total of 100 wt. % |

Example 7

Preparation of a Nano-Emulsion Composition of CoQ10

A nano-emulsion composition of CoQ10 was prepared by the same procedure as described in Example 1 except that the following constitutional composition for ingredients of the nano-emulsion composition was applied.

| | |
|---|---|
| CoQ10 | 5-20 wt. % |
| caprylic/capric glyceride | 20-30 wt. % |
| ethanol | 1-5 wt. % |
| glycerin | 10-20 wt. % |
| sugar esters | 1-6 wt. % |
| TEA cocoyl glutamate | 1-6 wt. % |
| water | The balance to make a total of 100 wt. % |

Example 8

Preparation of a Nano-Emulsion Composition of CoQ10

A nano-emulsion composition of CoQ10 was prepared by the same procedure as described in Example 1 except that the following constitutional composition for ingredients of the nano-emulsion composition was applied.

| | |
|---|---|
| CoQ10 | 5-20 wt. % |
| macadamia nut oil | 20-30 wt. % |
| ethanol | 1-5 wt. % |
| lecithin | 1-5 wt. % |
| glycerin | 10-20 wt. % |
| polysorbate 80 (polyoxyethylene 20 sorbitan monooleate) | 1-6 wt. % |
| water | The balance to make a total of 100 wt. % |

Example 9

Preparation of a Nano-Emulsion Composition of CoQ10

A nano-emulsion composition of CoQ10 was prepared by the same procedure as described in Example 1 except that the following constitutional composition for ingredients of the nano-emulsion composition was applied.

| | |
|---|---|
| CoQ10 | 5-20 wt. % |
| olive oil | 20-30 wt. % |
| ethanol | 1-5 wt. % |
| glycerin | 10-20 wt. % |
| glycerin fatty acid ester | 1-6 wt. % |
| sodium lauryl sulfate | 1-6 wt. % |
| water | The balance to make a total of 100 wt. % |

Example 10

Preparation of a Nano-Emulsion Composition of CoQ10

A nano-emulsion composition of CoQ10 was prepared by the same procedure as described in Example 1 except that the following constitutional composition for ingredients of the nano-emulsion composition was applied.

| | |
|---|---|
| CoQ10 | 5-20 wt. % |
| jojoba oil | 20-30 wt. % |
| ethanol | 1-5 wt. % |
| glycerin | 10-20 wt. % |
| polyglycerin fatty acid ester | 1-6 wt. % |
| sodium lauryl sulfate | 1-6 wt. % |
| water | The balance to make a total of 100 wt. % |

Example 11

Preparation of a Nano-Emulsion Composition of CoQ10

A nano-emulsion composition of CoQ10 was prepared by the same procedure as described in Example 1 except that the following constitutional composition for ingredients of the nano-emulsion composition was applied.

| | |
|---|---|
| CoQ10 | 5-20 wt. % |
| sunflower seed oil | 20-30 wt. % |
| ethanol | 1-5 wt. % |
| glycerin | 10-20 wt. % |
| propyleneglycol fatty acid ester | 1-9 wt. % |
| sodium lauryl sulfate | 1-3 wt. % |
| water | The balance to make a total of 100 wt. % |

Experimental Example 1

Observation of Characteristics of CoQ10

The compositions produced in Examples 1 to 11 were observed for phase separation, precipitation, stability and discoloration.

The prepared composition was subjected to visual inspection to determine whether there phase separation and/or the precipitation had occurred while, in order to determine stability, each of a number of samples of the compositions was stored at room temperature and in a thermostat of 45 C, respectively, to measure variation in concentration of CoQ10 in the sample. The results are shown in Table 1 below.

TABLE 1

| | | | Stability (the content of CoQ10, %) | | | | | |
|---|---|---|---|---|---|---|---|---|
| | | | room temperature | | | higher temperature (45° C.) | | |
| | phase separation | precipitation | The first stage | After 1 year | After 2 years | The first stage | After 1 year | After 2 years |
| Example 1 | good | Good | 100 | 100 | 100 | 100 | 100 | 100 |
| Example 2 | good | Good | 100 | 100 | 100 | 100 | 100 | 100 |
| Example 3 | good | Good | 100 | 100 | 100 | 100 | 100 | 100 |
| Example 4 | good | Good | 100 | 100 | 100 | 100 | 100 | 100 |
| Example 5 | good | Good | 100 | 100 | 100 | 100 | 100 | 100 |
| Example 6 | good | Good | 100 | 100 | 100 | 100 | 100 | 100 |
| Example 7 | good | Good | 100 | 100 | 100 | 100 | 100 | 100 |
| Example 8 | good | Good | 100 | 100 | 100 | 100 | 100 | 100 |
| Example 9 | good | Good | 100 | 100 | 100 | 100 | 100 | 100 |
| Example 10 | good | Good | 100 | 100 | 100 | 100 | 100 | 100 |
| Example 11 | good | Good | 100 | 100 | 100 | 100 | 100 | 100 |

While the compositions prepared in Examples 1 to 11 were stored at room temperature and a higher temperature such as 45 C, respectively for 2 years, each was subjected to monitoring of discoloration. As a result, it was demonstrated that all of the compositions exhibited essentially no color change.

Experimental Example 2

Pharmacokinetic Studies

In order to evaluate absorption ability of a nano-emulsion composition of CoQ10 according to the present invention, plasma concentration results obtained after IV or oral administration of the composition were subjected to pharmacokinetic analysis.

(1) Materials

A CoQ10 sample was obtained from the nano-emulsion composition of CoQ10 prepared in Example 1 and a CoQ10 powder formulation commercially available from Young-jin Pharm. Co., Ltd. was used as a control.

CoQ9 used as an internal reference material was purchased from Sigma Co. All other reagents used were HPLC grade or guaranteed-reagent (G.R.) grade. In this example, diethyl ether (Tedia Co., INC.), ACN and methanol (Fisher Scientific Co., Ltd.), and heparin (Upjohn., No. 268-5) of G.R. grade were also used.

An experiment was performed using various instruments including: an HPLC set (Jasco Co.: Model PU-980 pump, a LC-Net II control borwin integrator, a AS-950-10 autoinjector); a UV/VIS detector (Jasco Co.); a pH meter (DMS DP-800); a refrigerated centrifuge (Hitachi Co., Ltd., himac CR 15D); a desktop centrifuge (Beckman Industries Fullerton CA); a deep freezer (Scientemp Co., Ltd.); an ultrasonic cleaner (Mettler Electronics Co., Ltd.); a mechanical stirrer (Eurostar, IKA-Labortechnik Co.), a homogenizer (Ultra-Turrax T25, IKA-Labortechnik Co.), a centrifuge (GS-6KR Centrifuge) and the like.

Male Sprague Dawley® rats weighing 200 to 300 g were purchased from Samtaco (Ansung, Kyunggi-do, KOREA) as experimental animals. Each of the animals was placed in an empty cage under a specific environmental condition, in particular, at 23±2° C. with a relative humidity of 50±10%, a lighting cycle of 12 hr light/12 hr dark, ventilation ranging from 10 to 15 times/hr and an illumination intensity ranging from 150 to 300 Lux. The rats were given free access to feed (Samyang Oil & Feed Corp., Wonjoo, Kangwon-do, KOREA) and pure water through a filter and, after an acclimation period of about 1 week, used in the experiment.

(2) Establishment of Conditions for HPLC Analysis

In the experiment of the present invention, optimal conditions for HPLC analysis were established by performing a preliminary test and examinations described below, although HPLC analysis conditions for CoQ10 from biological samples have been reported. Various HPLC columns were examined with C-8 and C-18 reversed-phase HPLC. As a result, a Luna C18 column with dimensions of 4.6 mm×250 mm and a thickness of 5 μm was adopted because its analysis condition was excellent. A mobile phase solvent used in the column was a mixture of methanol, ethanol and 2-propanol in a relative ratio by volume of 55:20:25 (v/v %) as the optimal condition of the solvent, which was defined by regulating contents of individual solvents. A flow rate of the mobile phase was 1.0 mL/min. A UV detector was set to 275 nm at which maximum absorption peaks are indicated. After investigation of several compounds having similar structures, CoQ9 with excellent degree of separation was adopted as the internal reference material. As a result of studying and examining various types of solvents, 1-propanol with an excellent extraction ratio and superior reproducibility was determined as an extraction solvent to extract CoQ10 from the biological samples.

From results of HPLC analysis for plasma samples treated according to the procedure described in Experimental Method, a calibration curve for each of the samples is derived from the following equation:

$$y = 0.3034 \pm 0.00301 (R^2 = 0.9999)$$

The calibration curve was favorably linear within a range of 0.05 to 10 ug/mL and both within-day and between-day precision and accuracy were within 15%.

Accordingly, it is understood that this HPLC analysis for CoQ10 of the present invention has favorable features such as sufficient sensitivity, specificity, linearity, precision and accuracy for application to the following experiments.

(3) In vivo Pharmacokinetic Experiment after IV Administration and oral Administration In order to assess an absorption rate (bioavailability) of the nano-emulsion composition of CoQ10 of the present invention, a single IV injection and oral administrations for 5 consecutive days were conducted. A commercially available powder formulation was used as a control to compare its absorption rate to that of the present composition. The pharmacokinetic analysis for concentration results in plasma derived a final conclusion. In vivo CoQ10 concentration was measured using HPLC analysis.

1) Plasma Sampling after IV Administration

After lightly anesthetizing a number of rats with ether, polyethylene tubes PE-50 (Intramedic, Clay Adams, U.S.A) were inserted into a left femoral artery and a vein of each rat. When the rats recovered from the anesthesia, each of the nano-emulsion composition and the CoQ10 powder formulation (the control) was administered through the vein in an amount of 6 mg/kg. Then, blood samples were taken from the left femoral artery at 0 (blank), 1, 5, 10, 15, 30, 60, 90, 120 and 180 minutes. By centrifuging 2500 of the collected blood in a microfuge tube, 100 μl of the plasma was obtained and used for determination of CoQ10 concentration in plasma.

2) Plasma Sampling after Oral Administration

After oral administration of each of the present composition and CoQ10 powder formulation in an amount of 60 mg/kg for 4 days, each rat was lightly anesthetized with ether immediately before the administration at day 5. A polyethylene tube PE-50 (Intramedic, Clay Adams, U.S.A) was inserted into a left femoral artery of each rat. When the rat recovered from the anesthesia, each of the nano-emulsion composition and the CoQ10 powder formulation was orally administered in an amount of 60 mg/kg. Then, blood samples were taken from the left femoral artery at 0 (blank), 0.5, 1, 1.5, 2, 3, 4, 6, 8, 12, 18, 24 and 48 hours. By centrifuging 250 μl of the collected blood in a microfuge tube, 100 μl of the plasma was obtained and used for determination of CoQ10 concentration in plasma.

3) Determination of CoQ10 Concentration in Plasma

For CoQ10, a calibration curve with a favorable linear relation (R=0.999) within a range of 0.05 μg/mL to 10 μg/mL was made.

Figure 1:
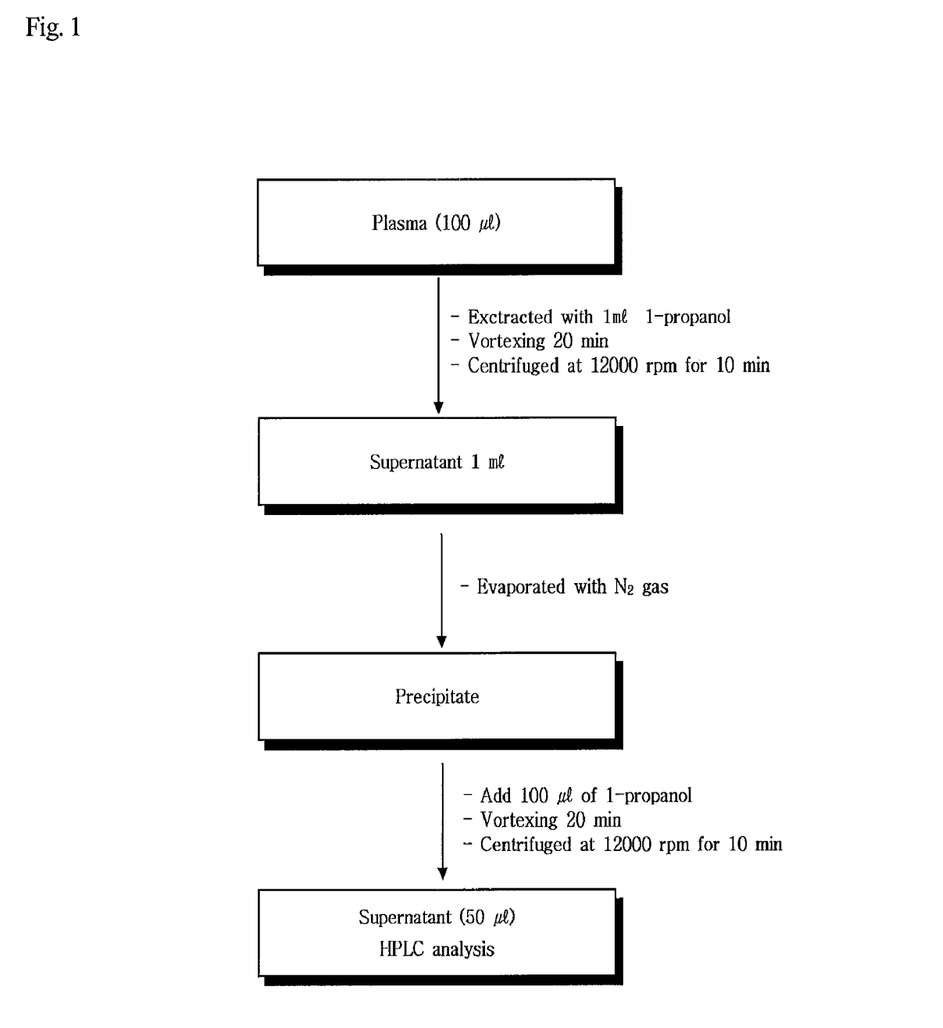
FIG. 1 schematically illustrates a procedure of preparing a plasma sample for HPLC assay of CoQ10 according to the present invention.

FIG. 1 schematically illustrates a procedure of preparing a plasma sample for HPLC assay of CoQ10 according to the present invention.

With regard to treatment of the samples, after adding 10 μL of 50 μM CoQ9 as an internal reference material and 1 ml of 1-propanol to 0.1 ml of the plasma sample, the mixture was subjected to extraction and sufficient admixing of the extracted material under vortex for 20 minutes, followed by centrifugation at 12,000 rpm for 10 minutes.

A supernatant was completely collected, transferred to an alternative micro tube to evaporate $N_2$ gas, and dissolved again in 100 μl of 1-propanol. From the resulting solution, 100 μL was sampled to determine CoQ10 concentration in plasma by HPLC analysis.

(4) Pharmacokinetic Analysis of Drug Concentration Change in Plasma

1) Estimation of Pharmacokinetic Parameters after IV Administration

Pharmacokinetic analysis was performed on plasma concentration-time data obtained after IV administration based on a linear 2-compartment model as follows:

Wherein $X_1$ and $X_2$ are amounts of drug in μg/ml in the circulatory system and peripheral compartments, respectively, $V_{d1}$ and $V_{d2}$ are volumes of distribution in ml/kg, and $k_{12}$, $k_{21}$ and $k_{e1}$ are rate constants between the compartments in $\min^{-1}$.

For the drug in each of the compartments, its mass balance can be obtained via the following equation:

[Formula 1]
$$\frac{dX_1}{dt} = -(k_{e1} + k_{12})X_1 + k_{21}X_2 \quad (1)$$

[Formula 2]
$$\frac{dX_2}{dt} = k_{21}X_1 - k_{21}X_2 \quad (2)$$

Solving the above equation for $X_1$ and dividing both sides of the equation by $V_{d1}$, a blood drug concentration C can be obtained via the following equation:

[Formula 3]
$$C = Ae^{-\alpha t} + Be^{-\beta t} \quad (3)$$

The plasma concentration-time data obtained after IV administration were fitted to the Formula 3 by a non-linear least square method to estimate some of the above parameters. Other kinetic parameters were determined by the following equations 4 to 8:

$$k_{21} = (A\beta + B\alpha)/(A+B) \quad \text{[Formula 4]}$$

$$k_{e1} = \frac{\alpha\beta}{k_{21}} \quad \text{[Formula 5]}$$

$$k_{12} = (\alpha + \beta) - (k_{21} + k_{e1}) \quad \text{[Formula 6]}$$

$$t_{1/2(\alpha)} = \frac{0.693}{\alpha} \quad \text{[Formula 7]}$$

$$t_{1/2(\beta)} = \frac{0.693}{\beta} \quad \text{[Formula 8]}$$

2) Estimation of Pharmacokinetic Parameters after Oral Administration

Pharmacokinetic analysis was performed on plasma concentration-time data obtained after oral administration based on a linear 1-compartment model which shows that the drug is absorbed at a first-order absorption rate from an absorption site as follows:

Wherein $X_a$ is an amount of drug in mg/kg at the absorption site, X is an amount of drug in mg/kg in a compartment in the body, $V_d$ is a volume of distribution in ml/kg, $k_a$ is an absorption rate constant in $\min^{-1}$, $k_{e1}$ is an elimination rate constant in $\min^{-1}$, and F is an absorption rate, respectively.

For the drug in each of the compartments, its mass balance can be obtained by the following equation:

$$\frac{dX_a}{dt} = -k_a \cdot X_a \quad \text{[Formula 9]}$$

$$\frac{dX}{dt} = k_a \cdot X_a - k_{e1} \cdot X \quad \text{[Formula 10]}$$

Solving the above equation for X and dividing both sides of the equation by $V_d$, a blood drug concentration C can be obtained by the following equation:

$$C = \frac{k_a \cdot F \cdot D}{Vd(k_a - k_{e1})}(e^{-ke1 \cdot t} + e^{-ka \cdot t}) \quad \text{[Formula 11]}$$

The plasma concentration-time data obtained after oral administration were fitted to the Formula 11 by a non-linear least square method to estimate the parameters $k_a$ and $k_{e1}$. Other kinetic parameters were determined by the following equations:

$$t_{1/2} = \frac{0.693}{k_{e1}} \quad \text{[Formula 12]}$$

3) Noncompartmental Analysis

With regard to estimation of certain parameters such as an area under a blood drug concentration curve AUC or AUMC, if a compartment model is presumed and set before the estimation, there may be significant differences between preset values by the compartment model and the estimated parameters. Therefore, the plasma concentration-time data obtained after IV and/or oral administration was used to determine the parameters by a noncompartmental method as follows:

$$AUC_t = \int_0^T C\,dt \quad \text{[Formula 13]}$$

$$AUC = \int_0^T C\,dt + C_T/k \quad \text{[Formula 14]}$$

$$AUMC = \int_0^\infty t \cdot C\,dt \quad \text{[Formula 15]}$$

$$MRT = \frac{AUMC}{AUC} \quad \text{[Formula 16]}$$

$$CL_t = \frac{F \cdot DOSE}{AUC} \quad \text{[Formula 17]}$$

$$Vdss = CL_t \cdot MRT \quad \text{[Formula 18]}$$

Wherein an area under a blood drug concentration curve till the last blood sampling time $AUC_t$ was calculated by a trapezoidal formula, areas under a blood drug concentration curve from zero to infinity for AUC and AUMC were calculated using a combination of extrapolation and the trapezoidal formula. MRT represents mean residence time, $CL_t$ represents systemic clearance and $V_{dss}$ represents steady-state volume of distribution.

(5) Results

1) CoQ10 Concentration Pattern in Plasma after IV Administration

Figure 2:
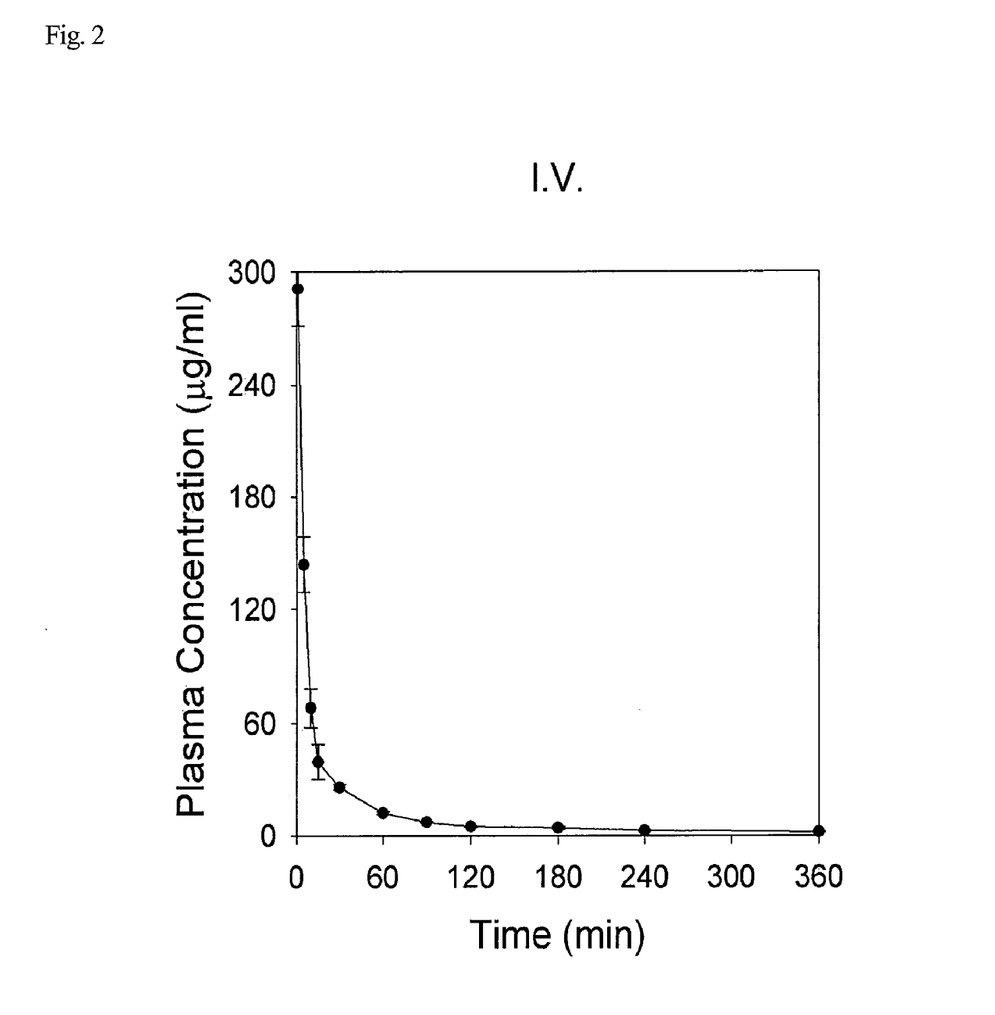
FIG. 2 is a plasma concentration-time curve after a single-dose IV administration of 6 mg/kg nano-emulsion composition of CoQ10 according to examples of the present invention in rats.

The nano-emulsion composition of CoQ10 according to examples of the present invention was administered IV to each of three rats in a single dose of 6 mg/kg, and the resulting plasma concentration-time data and Mean±S.E. of the results are presented in Tables 2 and 3, respectively. The pharmacokinetic parameters for the plasma concentration-time date and Mean±S.E. of the parameters are presented in Tables 4 and 5, respectively. FIG. 2 is a plasma concentration-time curve after a single-dose IV administration of 6 mg/kg nano-emulsion composition of CoQ10 according to examples of the present invention in rats.

From FIG. 2 and Tables 2 and 3, it was observed that the plasma concentration following IV administration of CoQ10 rapidly decreased at from zero to 60 minutes, followed by gradual reduction. A half life $t_{1/2,\alpha}$ at a phase before distribution "α phase" and another half life $t_{1/2,\beta}$ at a phase after distribution "β phase" were 3.3 min and 52 min, respectively (se Tables 4 and 5).

TABLE 2

| Time (min) | No. 1 | No. 2 | No. 3 | Mean | S.E. | C.V. (%) |
|---|---|---|---|---|---|---|
| 1 | 323 | 277 | 272 | 291 | 19.7 | 6.76 |
| 5 | 167 | 128 | 135 | 144 | 14.8 | 10.2 |
| 10 | 78.3 | 74.7 | 51.4 | 68.1 | 10.3 | 15.1 |
| 15 | 46.4 | 24.4 | 47.8 | 39.6 | 9.26 | 23.3 |
| 30 | 24.2 | 25.7 | 28.2 | 26.1 | 1.44 | 5.54 |
| 60 | 13.1 | 11.6 | — | 12.4 | 0.782 | 6.31 |
| 90 | 7.51 | 6.99 | 7.77 | 7.42 | 0.279 | 3.75 |
| 120 | 5.57 | 4.58 | 4.85 | 5.00 | 0.362 | 7.23 |
| 180 | 3.96 | 3.13 | 5.32 | 4.14 | 0.780 | 18.8 |
| 240 | N.D.[a] | 2.13 | 3.17 | 2.65 | 0.517 | 19.4 |
| 360 | N.D. | 1.71 | 2.30 | 2.01 | 0.299 | 14.9 |

*N.D.: Not Detected (below the Quantitation).

TABLE 3

| Time (min) | Plasma concentration (µg/ml) |
|---|---|
| 1 | 291.05 ± 19.702 |
| 5 | 144.02 ± 14.823 |
| 10 | 68.17 ± 10.332 |
| 15 | 39.61 ± 9.268 |
| 30 | 26.09 ± 1.447 |
| 60 | 12.41 ± 0.782 |
| 90 | 7.43 ± 0.279 |
| 120 | 5.00 ± 0.362 |
| 180 | 4.14 ± 0.780 |
| 240 | 2.65 ± 0.517 |
| 360 | 2.00 ± 0.299 |

TABLE 4

| Parameter | No. 1 | No. 2 | No. 3 | Mean | S.E. | C.V. (%) |
|---|---|---|---|---|---|---|
| A (µg/ml) | 353 | 316 | 301 | 324 | 18.9 | 5.84 |
| B (µg/ml) | 32.3 | 22.6 | 40.8 | 31.9 | 6.41 | 20.1 |
| α (min$^{-1}$) | 0.191 | 0.210 | 0.245 | 0.215 | 0.0193 | 8.98 |
| β (min$^{-1}$) | 0.0143 | 0.0111 | 0.0154 | 0.0136 | 0.00156 | 11.4 |
| $K_{12}$ (min$^{-1}$) | 0.0830 | 0.101 | 0.130 | 0.104 | 0.0168 | 16.1 |
| $K_{21}$ (min$^{-1}$) | 0.0291 | 0.0244 | 0.0428 | 0.0321 | 0.00673 | 20.9 |
| $K_{el}$ (min$^{-1}$) | 0.0938 | 0.0956 | 0.0881 | 0.0925 | 0.00277 | 2.99 |
| $t_{1/2\alpha}$ (min) | 3.62 | 3.30 | 2.83 | 3.25 | 0.283 | 8.71 |
| $t_{1/2\beta}$ (min) | 48.5 | 62.3 | 45.1 | 51.9 | 6.44 | 12.3 |
| AUC (µg · min ml$^{-1}$) | 4340 | 3960 | 4830 | 4380 | 308 | 7.03 |
| MRT (min) | 49.5 | 78.3 | 127 | 84.9 | 27.7 | 32.6 |
| Vdss (ml/kg) | 68.3 | 119 | 158 | 115 | 31.7 | 27.6 |
| CLt (ml/min) | 1.38 | 1.51 | 1.24 | 1.39 | 0.0962 | 6.98 |

*N.D.: Not Detected (below the Quantitation).

TABLE 5

| Parameter | Dose |
|---|---|
| A (µg/ml) | 323 ± 18.9 |
| B (µg/ml) | 31.9 ± 6.41 |
| α (min$^{-1}$) | 0.215 ± 0.0193 |
| β (min$^{-1}$) | 0.0135 ± 0.00155 |
| $K_{12}$ (min$^{-1}$) | 0.104 ± 0.0167 |
| $K_{21}$ (min$^{-1}$) | 0.0321 ± 0.00673 |
| $K_{el}$ (min$^{-1}$) | 0.0925 ± 0.00277 |
| $t_{1/2\alpha}$ (min) | 3.250 ± 0.283 |
| $t_{1/2\beta}$ (min) | 51.9 ± 6.44 |
| AUC (µg · min ml$^{-1}$) | 3793 ± 193 |
| MRT (min) | 84.9 ± 27.6 |
| Vdss (ml/kg) | 114.8 ± 31.6 |
| CLt (ml/min) | 1.378 ± 0.0961 |

2) CoQ10 Concentration Pattern in Plasma after Oral Administration

The nano-emulsion composition of CoQ10 according to examples of the present invention was orally administered to each of three rats at a dose of 60 mg/kg daily for 5 consecutive days, and the resulting plasma concentration-time data and Mean±S.E. of the results are presented in Tables 6 and 7, respectively.

Figure 3:
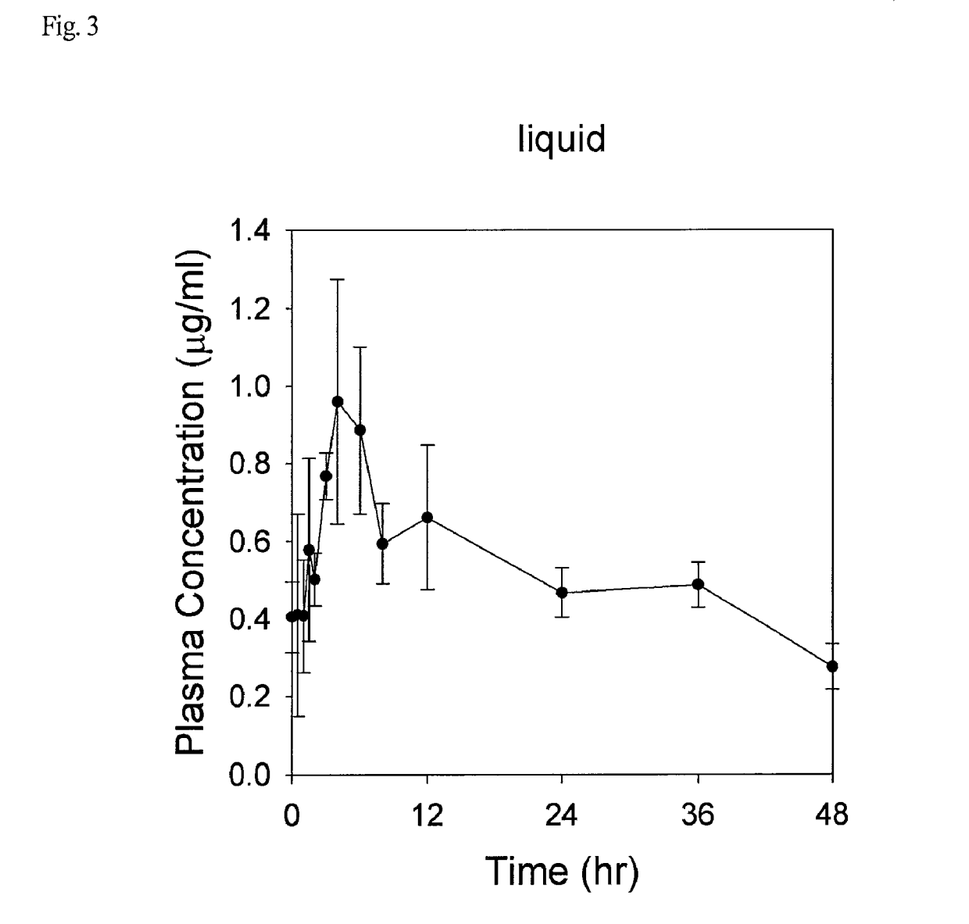
FIG. 3 is a plasma concentration-time curve after multiple-dose oral administration of 60 mg/kg nano-emulsion composition of CoQ10 according to examples of the present invention in rats.

FIG. 3 is a plasma concentration-time curve after multiple-dose oral administration of 60 mg/kg nano-emulsion composition of CoQ10 according to examples of the present invention in rats.

TABLE 6

| Time (hr) | No. 1 | No. 2 | No. 3 | Mean | S.E. | C.V. (%) |
|---|---|---|---|---|---|---|
| 0 | 0.501 | 0.321 | 0.268 | 0.363 | 0.086 | 23.760 |
| 0.5 | 0.481 | 0.065 | 0.198 | 0.248 | 0.150 | 60.618 |
| 1 | 0.521 | 0.107 | 0.442 | 0.357 | 0.155 | 43.520 |
| 1.5 | — | 0.274 | 0.524 | 0.399 | 0.125 | 31.258 |
| 2 | — | 0.562 | 0.552 | 0.557 | 0.005 | 0.872 |
| 3 | 0.643 | 0.806 | 0.832 | 0.760 | 0.073 | 9.536 |
| 4 | 0.892 | 0.725 | 1.605 | 1.074 | 0.331 | 30.779 |
| 6 | 1.039 | 0.678 | 1.236 | 0.984 | 0.200 | 20.333 |
| 8 | 0.732 | 0.391 | 0.598 | 0.573 | 0.122 | 21.225 |
| 12 | 0.651 | 0.367 | 0.620 | 0.546 | 0.110 | 20.178 |
| 18 | 0.470 | 0.341 | 0.554 | 0.455 | 0.076 | 16.619 |
| 24 | 0.515 | — | 0.394 | 0.455 | 0.060 | 13.259 |
| 48 | 0.334 | 0.216 | N.D.[a] | 0.275 | 0.059 | 21.387 |

*N.D.: Not Detected (below the Quantitation).

TABLE 7

| Time (hr) | Plasma concentration (µg/ml) |
|---|---|
| 0 | 0.36 ± 0.086 |
| 0.5 | 0.25 ± 0.150 |
| 1 | 0.36 ± 0.155 |
| 1.5 | 0.40 ± 0.125 |
| 2 | 0.56 ± 0.005 |
| 3 | 0.76 ± 0.073 |
| 4 | 1.07 ± 0.331 |
| 6 | 0.98 ± 0.200 |
| 8 | 0.57 ± 0.122 |
| 12 | 0.55 ± 0.110 |
| 24 | 0.45 ± 0.076 |
| 36 | 0.45 ± 0.060 |
| 48 | 0.28 ± 0.059 |

A CoQ10 powder formulation as a control was orally administered to each of two rats at a dose of 60 mg/kg daily for 5 consecutive days, and the resulting plasma concentration-time data and Mean±S.E. of the results are presented in Tables 8 and 9, respectively.

Figure 4:
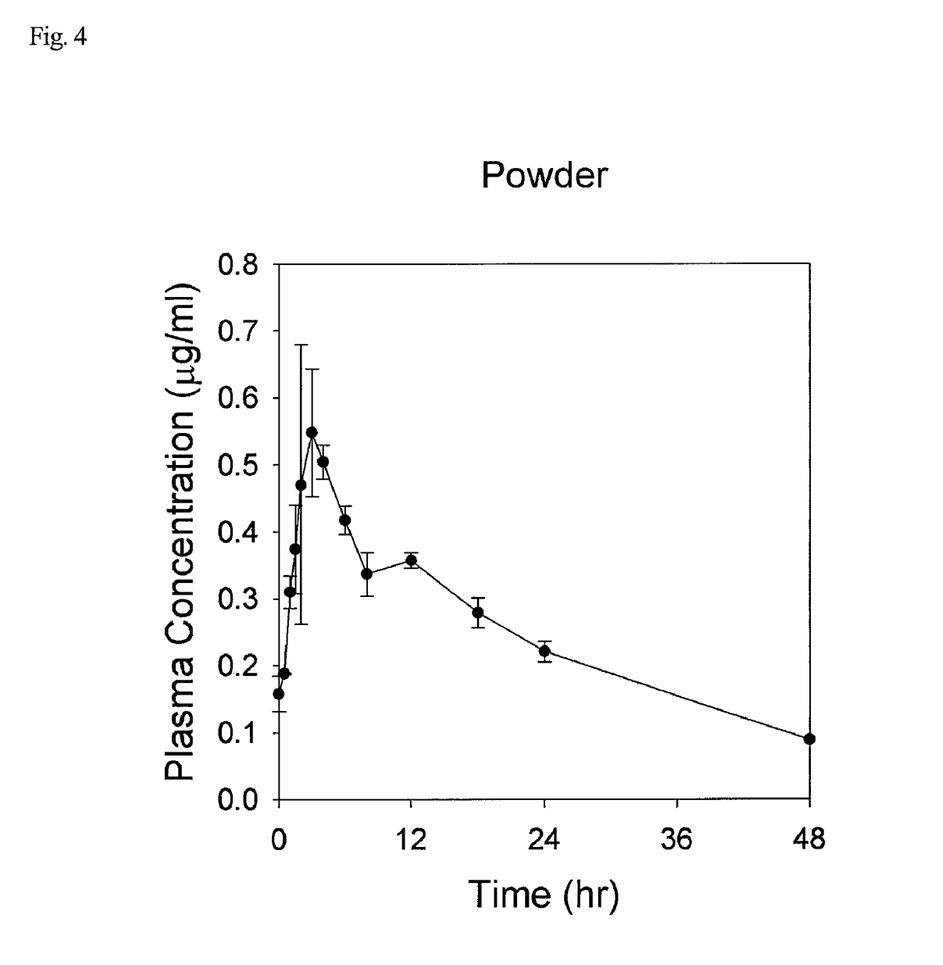
FIG. 4 is a plasma concentration-time curve after multiple-dose oral administration of 60 mg/kg CoQ10 powder formulation, as a control, in rats.

FIG. 4 is a plasma concentration-time curve after multiple-dose oral administration of 60 mg/kg CoQ10 powder formulation, as a control, in rats,

TABLE 8

| Time (hr) | No. 1 | No. 2 | Mean | S.E. | C.V. (%) |
|---|---|---|---|---|---|
| 0 | 0.133 | 0.184 | 0.158 | 0.026 | 16.14 |
| 0.5 | 0.189 | 0.187 | 0.188 | 0.001 | 0.650 |
| 1 | 0.334 | 0.285 | 0.310 | 0.025 | 7.925 |
| 1.5 | 0.440 | 0.308 | 0.374 | 0.066 | 17.69 |
| 2 | 0.679 | 0.262 | 0.471 | 0.209 | 44.32 |
| 3 | 0.643 | 0.453 | 0.548 | 0.095 | 17.31 |
| 4 | 0.529 | 0.479 | 0.504 | 0.025 | 4.932 |
| 6 | 0.439 | 0.396 | 0.417 | 0.022 | 5.159 |
| 8 | 0.304 | 0.370 | 0.337 | 0.033 | 9.800 |
| 12 | 0.369 | 0.346 | 0.357 | 0.012 | 3.239 |
| 18 | 0.301 | 0.255 | 0.278 | 0.023 | 8.248 |
| 24 | 0.205 | 0.236 | 0.220 | 0.015 | 6.907 |
| 48 | N.D.[a)] | 0.089 | 0.089 | | |

*N.D.: Not Detected (below the Quantitation).

TABLE 9

| Time (hr) | Plasma concentration (µg/ml) |
|---|---|
| 0 | 0.16 ± 0.026 |
| 0.5 | 0.19 ± 0.001 |
| 1 | 0.31 ± 0.025 |
| 1.5 | 0.37 ± 0.066 |
| 2 | 0.47 ± 0.209 |
| 3 | 0.55 ± 0.095 |
| 4 | 0.50 ± 0.025 |
| 6 | 0.42 ± 0.022 |
| 8 | 0.34 ± 0.033 |
| 12 | 0.36 ± 0.012 |
| 18 | 0.28 ± 0.023 |
| 24 | 0.22 ± 0.015 |
| 48 | 0.089 |

Furthermore, pharmacokinetic parameters for the results shown in Tables 6 and 8 are given in Tables 10 and 11, while Mean±S.E. of the parameters are shown in Table 12.

TABLE 10

| | No. 1 | No. 2 | No. 3 | Mean | S.E. | C.V. (%) |
|---|---|---|---|---|---|---|
| AUC (µg · hr ml$^{-1}$) | 32.5 | 36.6 | 31.3 | 33.5 | 1.96 | 5.85 |
| $C_{max}$ (µg/hr) | 1.04 | 0.806 | 1.60 | 1.15 | 0.29 | 25.3 |
| $T_{max}$ (hr) | 6.00 | 3.00 | 4.00 | 4.33 | 1.08 | 24.9 |
| ka (hr$^{-1}$) | 0.13 | 0.152 | 0.096 | 0.126 | 0.02 | 15.9 |
| $t_{1/2}$ (hr) | 7.05 | 16.4 | 11.2 | 11.5 | 3.33 | 28.8 |
| AUMC (µg · hr$^2$ ml$^{-1}$) | 59.5 | 563 | 222 | 281 | 182 | 64.6 |
| MRT (hr) | 12.26 | 33.0 | 15.7 | 20.3 | 7.86 | 38.7 |
| Vdss (ml/kg) | 68300 | 55400 | 29900 | 51200 | 138000 | 27.0 |
| CLt (ml/hr) | 5570 | 1630 | 1910 | 3030 | 1550 | 51.2 |
| BA (%) | 4.46 | 5.01 | 4.29 | 4.59 | 0.269 | 5.85 |

TABLE 11

| | No. 1 | No. 2 | Mean | S.E. | C.V. (%) |
|---|---|---|---|---|---|
| AUC (µg · hr ml$^{-1}$) | 13.1 | 13.8 | 13.4 | 0.346 | 2.58 |
| $C_{max}$ (µg/hr) | 0.679 | 0.479 | 0.579 | 1.00 | 173 |
| $T_{max}$ (hr) | 2.00 | 4.00 | 3.00 | 1.00 | 33.3 |
| ka (hr$^{-1}$) | 0.592 | 0.199 | 0.395 | 0.196 | 49.6 |
| $t_{1/2}$ (hr) | 7.91 | 4.99 | 6.45 | 1.46 | 22.6 |
| AUMC (µg · hr$^2$ ml$^{-1}$) | 85.3 | 53.7 | 69.5 | 15.8 | 22.8 |
| MRT (hr) | 13.7 | 13.9 | 13.8 | 0.075 | 0.542 |
| Vdss (ml/kg) | 9310 | 15100 | 12200 | 2910 | 23.8 |
| CLt (ml/hr) | 677 | 1090 | 883 | 205 | 23.3 |
| BA (%) | 1.79 | 1.89 | 1.84 | 0.0475 | 2.58 |

TABLE 12

| | Dose | |
|---|---|---|
| Parameter | Solution | Powder |
| AUC (µg · hr ml$^{-1}$) | 33.4 ± 1.96 | 13.4 ± 0.346 |
| $C_{max}$ (µg/hr) | 1.15 ± 0.291 | 0.579 ± 1.00 |
| $T_{max}$ (hr) | 4.33 ± 1.080 | 3.00 ± 1.00 |
| ka (hr$^{-1}$) | 0.126 ± 0.020 | 0.395 ± 0.196 |
| $t_{1/2}$ (hr) | 11.5 ± 3.33 | 6.45 ± 1.46 |
| AUMC (µg · hr$^2$ ml$^{-1}$) | 281 ± 181 | 69.4 ± 15.8 |
| MRT (hr) | 20.3 ± 7.86 | 13.8 ± 0.075 |
| Vdss (ml/kg) | 51200 ± 13800 | 12200 ± 2913 |
| CLt (ml/hr) | 3030 ± 1550 | 882 ± 205 |
| BA (%) | 4.59 | 1.84 |

Table 12 shows that maximum plasma concentration $C_{max}$ after oral administration of the nano-emulsion composition according to the present invention was about 2 times higher than that of the control and the half life $t_{1/2}$ of the present composition also was about 2 times longer than that of the control.

The nano-emulsion composition of the present invention had a higher $C_{max}$ and a longer $t_{1/2}$ than the control powder formulation and, as a result, AUC of the present composition was about 2.5 times larger than that of the control.

From the results described above, it is clearly understood that the nano-emulsion composition according to the present invention can exhibit improved bioavailability after oral administration thereof, compared to the control CoQ10 powder formulation.

[Industrial Applicability]

As apparent from the above description, a composition of the present invention which can be completely dissolved in water has an advantage that the composition is conveniently applied to production of drinks and/or other formulations for oral administration.

A nano-emulsion composition of CoQ10 of the present invention is preferably applicable to pharmaceutical formulations for oral administration or food products and, especially, to manufacture of tonic drinks and/or functional health beverages. For these purposes, the present inventive composition may be diluted in water for use.

The invention claimed is:

1. A nano-emulsion composition of CoQ1O comprising 5 to 20 wt. % of CoQ1O; 1 to 5 wt. % of ethanol; 1 to 5 wt. % of lecithin; 20 to 30 wt. % of caprylic/capric glyceride; 10 to 20 wt. % of glycerin; 1 to 15 wt. % of at least two coemulsifiers selected from the group consisting of polysorbate 20 (polyoxyethylene 20 sorbitan monolaurate), polysorbate 80 (polyoxyethylene 20 sorbitan monooleate), anionic amino acid based emulsifier(s), polyglycerin fatty acid ester, glycerin fatty acid ester, propyleneglycol fatty acid ester, sugar esters, cholesterol and sodium lauryl sulfate; and the balance of water.

2. The nano-emulsion composition as claimed in claim 1, wherein the anionic amino acid based emulsifier(s) is at least one selected from a group consisting of: TEA cocoyl glutamate; sodium glutamate; sodium cocoyl glutamate; magnesium cocoyl glutamate; and sodium lauroyl glutamate.

3. The nano-emulsion composition as claimed in claim 1, wherein the composition has a viscosity ranging from 1.0 to 15cPs(centipoises).

4. A nano-emulsion composition of CoQ10 comprising 5 to 20 wt. % of CoQ10; 1 to 5 wt. % of ethanol; 20 to 30 wt. % of caprylic/capric glyceride; 1 to 25 wt. % of at least two emulsifiers selected from the group consisting of polysorbate 20 (polyoxyethylene 20 sorbitan monolaurate), polysorbate 80 (polyoxyethylene 20 sorbitan monooleate), anionic amino acid based emulsifier(s), polyglycerin fatty acid ester, glycerin fatty acid ester, propyleneglycol fatty acid ester, sugar esters, cholesterol and sodium lauryl sulfate; 10 to 20 wt. % of glycerin and the balance of water.

5. The nano-emulsion composition as claimed in claim 4, wherein the anionic amino acid based emulsifier(s) is at least one selected from the group consisting of: TEA cocoyl glutamate; sodium glutamate; sodium cocoyl glutamate; magnesium cocoyl glutamate; and sodium lauroyl glutamate.

6. The nano-emulsion composition as claimed in claim 4, wherein the composition has a viscosity ranging from 1.0 to 15cPs(centipoises).

* * * * *